(12) United States Patent
Yonezawa

(10) Patent No.: US 8,244,362 B2
(45) Date of Patent: Aug. 14, 2012

(54) VISION REGENERATION ASSISTING APPARATUS

(75) Inventor: Eiji Yonezawa, Okazaki (JP)

(73) Assignee: Nidek Co., Ltd., Aichi (JP)

( * ) Notice: Subject to any disclaimer, the term of this patent is extended or adjusted under 35 U.S.C. 154(b) by 1158 days.

(21) Appl. No.: 11/393,839

(22) Filed: Mar. 31, 2006

(65) Prior Publication Data
US 2006/0287688 A1 Dec. 21, 2006

(30) Foreign Application Priority Data

Mar. 31, 2005 (JP) ................ P2005-100560

(51) Int. Cl.
*A61N 1/08* (2006.01)
(52) U.S. Cl. .......................... 607/53; 607/54
(58) Field of Classification Search ............. 607/53–54, 607/59
See application file for complete search history.

(56) References Cited

U.S. PATENT DOCUMENTS

| | | | | |
|---|---|---|---|---|
| 4,510,936 A | * | 4/1985 | Fourcin et al. | 607/57 |
| 4,510,939 A | * | 4/1985 | Brenman et al. | 600/384 |
| 5,507,785 A | * | 4/1996 | Deno | 607/24 |
| 5,935,155 A | * | 8/1999 | Humayun et al. | 607/54 |
| 2002/0161417 A1 | * | 10/2002 | Scribner | 607/54 |
| 2004/0098067 A1 | | 5/2004 | Ohta et al. | |
| 2004/0102843 A1 | | 5/2004 | Yagi | |
| 2004/0116980 A1 | | 6/2004 | Ohta et al. | |
| 2004/0193232 A1 | | 9/2004 | Yagi et al. | |

FOREIGN PATENT DOCUMENTS

| | | |
|---|---|---|
| JP | 62-122662 A | 6/1987 |
| JP | 2004-298298 A | 10/2004 |
| WO | WO 02/064072 A1 | 8/2002 |
| WO | WO 02/067829 A1 | 9/2002 |
| WO | WO 02/080828 A1 | 10/2002 |
| WO | 03/067516 A2 | 8/2003 |

OTHER PUBLICATIONS

Japanese Office Action, dated Sep. 15, 2010, issued in counterpart application No. 2005100560.

* cited by examiner

*Primary Examiner* — Niketa Patel
*Assistant Examiner* — Hiba El-Kaissi
(74) *Attorney, Agent, or Firm* — Sughrue Mion, PLLC

(57) ABSTRACT

Provided is a vision regeneration assisting apparatus including a plurality of electrodes which are placed in a human body to apply an electrostimulation pulse signal to a cell for forming a retina; and a controller which outputs the electrostimulation pulse signal having bipolarity from the electrodes, wherein the controller comprises a capacitor which accumulates a current used for the electrostimulation pulse signal and converts the current into a voltage; a voltage detecting circuit which detects the voltage of a capacitor; and a switching circuit which allows the current to flow in the electrodes until the voltage of the capacitor reaches a predetermined voltage and allows the current having polarity opposite to (the polarity of the current which flows until the voltage of the capacitor reaches the predetermined voltage) until the voltage of the capacitor is substantially reset to 0.

7 Claims, 5 Drawing Sheets

2

VISION REGENERATION ASSISTING APPARATUS

BACKGROUND OF THE INVENTION (1) Field of the Invention

The present invention relates to an apparatus for assisting a regeneration of a vision.

(2) Background Art

A vision regeneration assisting apparatus (performing a portion of a lost vision function) for applying electrostimulation (outputting an electrostimulation pulse signal) to a cell that forms a retina (hereinafter, referred to as a retina cell) using an electrode placed in a human body has been suggested. In such an apparatus, it is a need for stabilizing an operation on an optic nerve.

SUMMARY OF THE INVENTION

It is an object of the present invention to provide a vision regeneration assisting apparatus capable of suppressing power loss and maintaining balance between negative and positive charges in a bipolar electrostimulation pulse signal upon stimulation.

In order to solve the above-described problems, the present invention has the following configuration.

(1) A vision regeneration assisting apparatus for assisting a regeneration of a vision of a patient, comprising:

a plurality of electrodes which are placed in a human body to apply an electrostimulation pulse signal to a cell that forms a retina; and a controller which causes the plurality of electrodes to output the electrostimulation pulse signal having bipolarity, wherein the controller includes:

a capacitor which accumulates a current used for the electrostimulation pulse signal and converts the current into a voltage;

a voltage detecting circuit which detects the voltage of a capacitor; and a switching circuit which allows the current to flow in the electrodes until the voltage of the capacitor reaches a predetermined voltage and allows the current having polarity, which is opposite to the polarity of the current which flows until the voltage of the capacitor reaches the predetermined voltage, until the voltage of the capacitor is substantially reset to 0.

(2) The vision regeneration assisting apparatus according to (1), wherein the voltage detecting circuit includes a buffer which detects the voltage without affecting the voltage of the capacitor.

(3) The vision regeneration assisting apparatus according to (2) further comprising a multiplexer which sequentially outputs electrostimulation pulse signals from the electrodes.

(4) The vision regeneration assisting apparatus according to (1) further comprising a transmitting/receiving unit which transmits data for an electrostimulation pulse signal to the controller.

(5) The vision regeneration assisting apparatus according to (4) further comprising:

a photographing unit which photographs an object at the outside a human body; and a processing unit which processes image data obtained by the photographing unit and converts the image data into the data for the electrostimulation pulse signal.

PREFERRED EMBODIMENTS OF THE INVENTION

Figure 1:
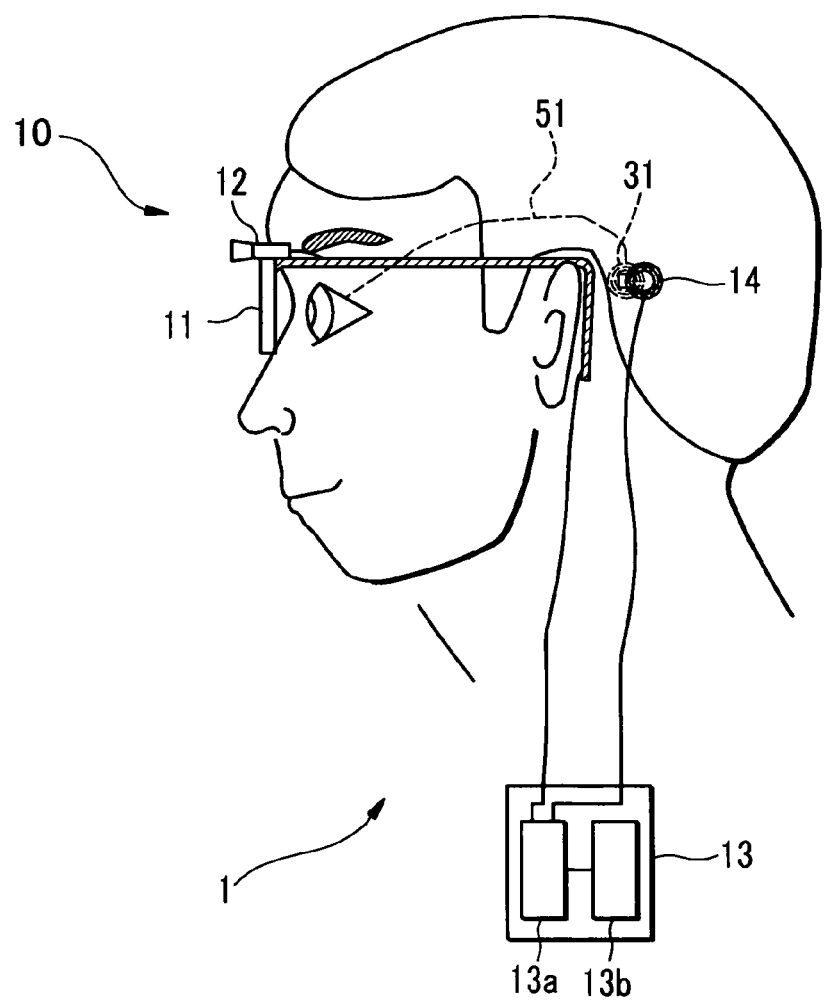
FIG. 1 is a view showing a schematic structure of a vision regeneration assisting apparatus according to an embodiment of the present invention.
Figure 2:
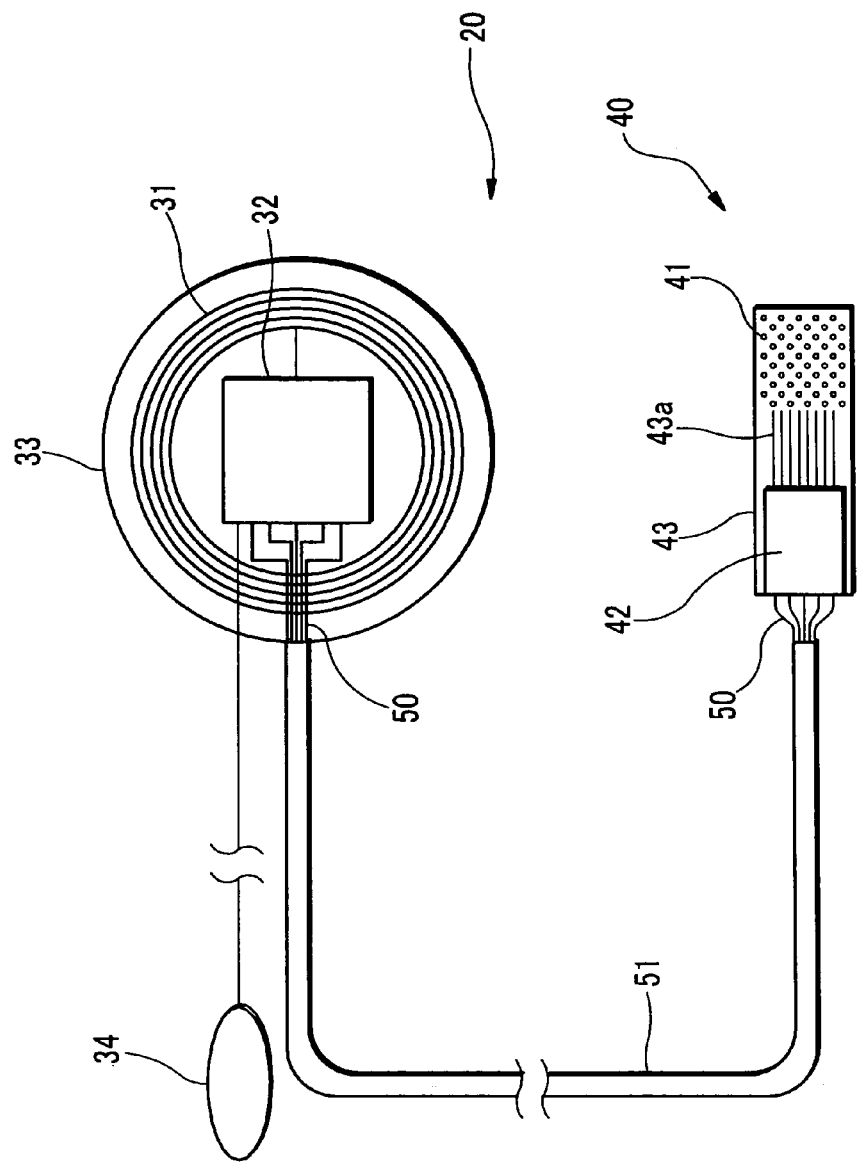
FIG. 2 is a view showing a schematic structure of an internal device of the vision regeneration assisting apparatus.
Figure 3:
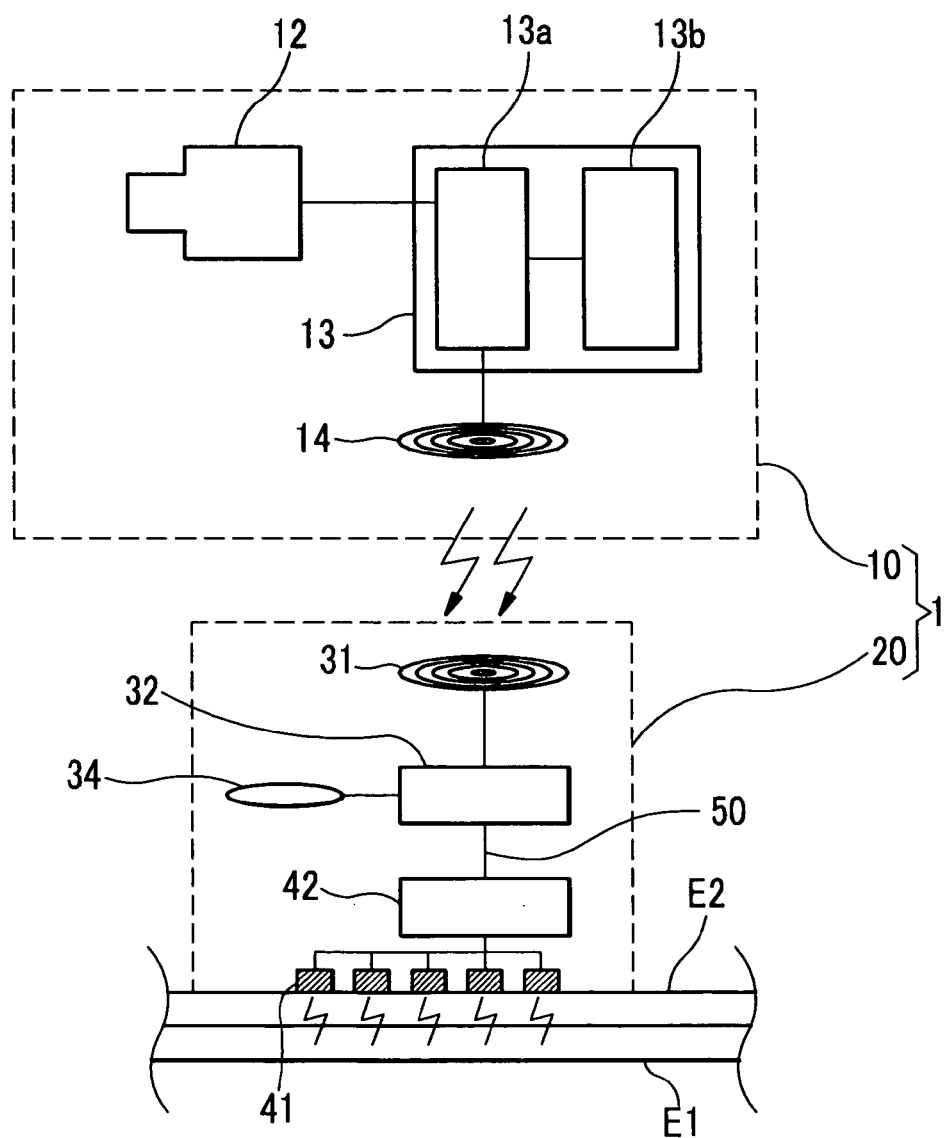
FIG. 3 is a schematic block diagram of the vision regeneration assisting apparatus.

Hereinafter, an embodiment of the present invention will be described with reference to the attached drawings. FIG. 1 is a view showing a schematic structure of a vision regeneration assisting apparatus according to an embodiment of the present invention, FIG. 2 is a view showing a schematic structure of an internal device of the vision regeneration assisting apparatus, and FIG. 3 is a schematic block diagram of the vision regeneration assisting apparatus.

A vision regeneration assisting apparatus 1 includes an external device 10 for photographing an external object to obtain image data and obtaining electrostimulation data and an internal device 20 for applying electrostimulation to a retina cell.

The external device 10 includes a visor 11 which a patient wears, a photographing unit 12 having a CCD camera attached to the visor 11, an external unit 13, and a transmitting unit 14 having a primary coil. The visor 11 has an eyeglass shape and is placed in front of the patient's eyes. The photographing unit 12 is attached to the front surface of the visor 11 to photograph an object to be recognized by the patient.

The external unit 13 includes a processing unit 13a having an arithmetic processing circuit such as a central processing unit (CPU) and performing image process and signal conversion, and a power supply unit 13b for supplying power to the apparatus 1 (the external device 10 and the internal device 20). The processing unit 13a performs image-processing on the image data obtained by the photographing unit 12 and converts the image data into data for an electrostimulation pulse signal. The transmitting unit 14 transmits the data for the electrostimulation pulse signal converted by the processing unit 13a and the power supplied from the power supply unit 13b to the internal device 20 as an electromagnetic wave. A magnet (not shown) used for alignment with a below-described receiving unit 31 is attached to the central portion of the transmitting unit 14.

The internal device 20 includes the receiving unit 31 having a secondary coil for receiving the data for the electrostimulation pulse signal and the power transmitted from the external device 10, a controller 32, an indifferent electrode 34, and an electrostimulating unit 40 for electrostimulating the retina cell. The controller 32 divides the data for the electrostimulation pulse signal and the power, converts the data for the electrostimulation pulse signal into the electrostimulation pulse signal, and transmits the electrostimulation pulse signal to the stimulating unit 40. The receiving unit 31 and the controller 32 are disposed on a substrate 33. A magnet (not shown) used for alignment with the transmitting unit 14 is attached to the central portion of the transmitting unit 13.

The controller 32 has a circuit configuration capable of suppressing power loss and maintaining balance between negative and positive charges in a biphasic pulse signal (bipolar pulse signal having negative and positive current values) upon stimulation (This will be later described in detail).

The stimulating unit 40 includes a plurality of electrodes 41 for outputting the electrostimulation pulse signal and a multiplexer 42. The electrodes 41 are disposed on a substrate 43. The multiplexer 42 is disposed (flip-chip mounted) on the substrate 43. The substrate 43 is made of a material which can be bent in a predetermined thickness with good biocompatibility, such as polypropylene or polyimide, and has a substantially elongated plate shape. A lead wire 43a for electrically connecting the electrodes 41 and the multiplexer 42 is formed on the substrate 43.

The controller 32 and the multiplexer 42 are electrically connected to each other with a plurality of wires 50. The wires 50 are bundled with a tube 51.

Figure 4:
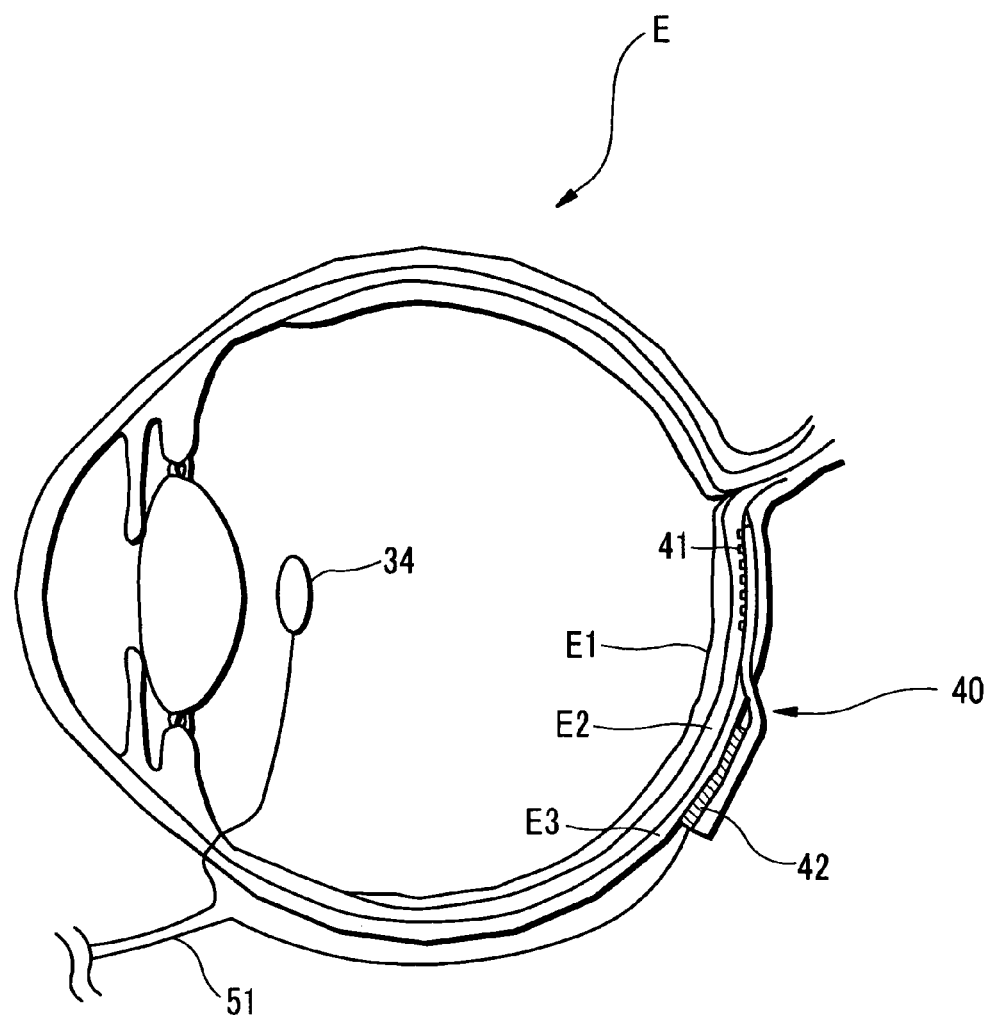
FIG. 4 is a view showing a state where an electrostimulating unit is placed in a human body.

As shown in FIG. 4, the electrodes 41 of the stimulating unit 40 are placed between a choroid E2 and a sclera E3 to be in contact with the choroid E2 and the multiplexer 42 of the stimulating unit 40 is placed outside the sclera E3. The indifferent electrode 34 is placed in the eye E of the patient through the sclera E3 and so on.

The receiving unit 31 is placed at a position for receiving the signal from the transmitting unit 14. As shown in FIG. 1, the receiving unit is, for example, placed under the skin of the side of the head of the patient. The transmitting unit 14 is placed at a position facing the receiving unit 31 through the skin. Since the transmitting unit 14 and the receiving unit 31 are attached to each other with the magnet, the transmitting unit 14 and the receiving unit 31 are magnetically attached to each other and the transmitting unit 14 is held on the side of the head.

The tube 51 (wire 50) which extends from the controller 32 provided in the receiving unit 31 perforates through the skin of the side of the head (see FIG. 1), and is inserted into an eye socket through the inside of the eyelid and connected to the multiplexer 42 through the outside of the sclera E3 (see FIG. 4).

Although, in the present embodiment, the electrodes 41 of the stimulating unit 40 are placed between the choroid E2 and the sclera E3 such that the cell that forms the retina E1 is subjected to the electrostimulation from the outside of the choroid E2, the present invention is not limited thereto. The electrodes may be placed at any position in which the cell that forms the retina E1 can be subjected to the electrostimulation. For example, the electrodes 41 of the stimulating unit 40 may be placed between the retina E1 and the choroid E2 or on the retina E1.

Figure 5:
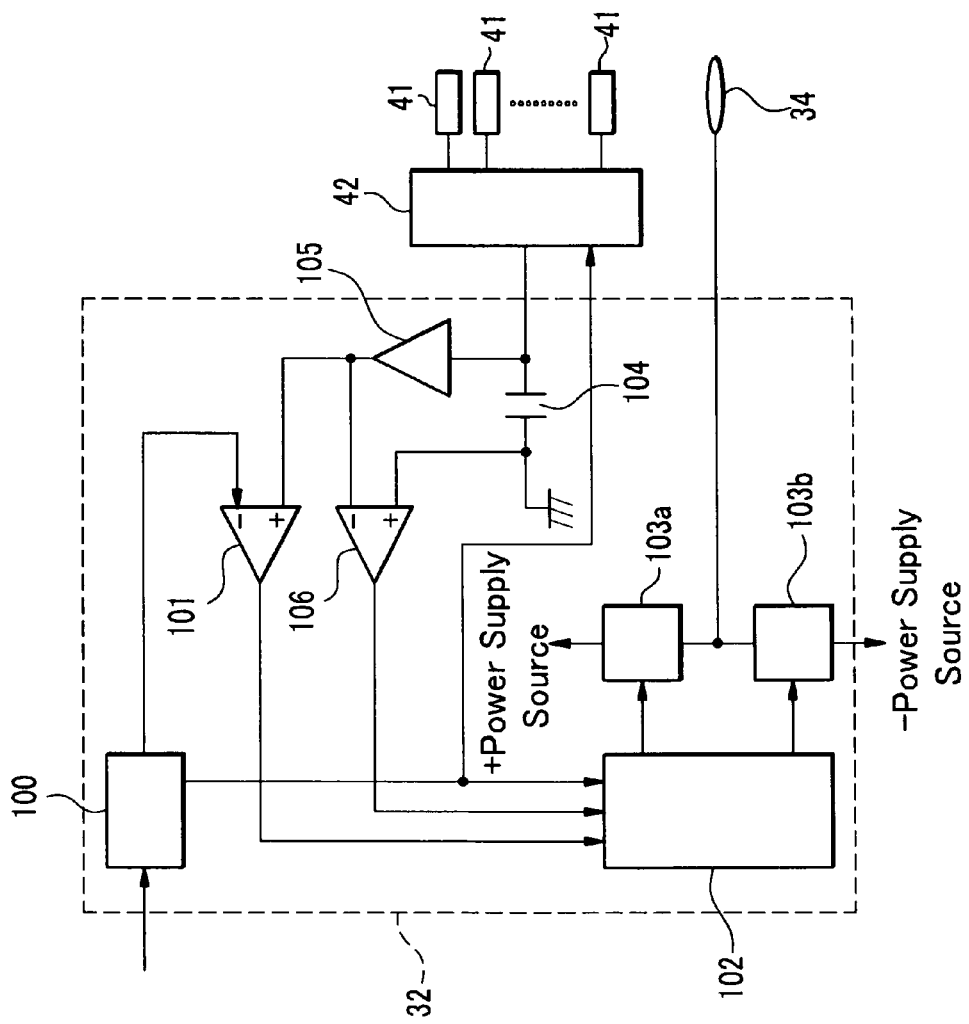
FIG. 5 is a circuit diagram of a controller.

FIG. 5 is a circuit diagram of the controller 32. A converting circuit 100 divides the data for the electrostimulation pulse signal and the power received by the receiving unit 31 and generates a stimulation strength instruction signal, an electrode specifying (electrode selecting) signal and so on of the electrostimulation pulse signal based on the data for the electrostimulation pulse signal. The electrode specifying signal is input to the multiplexer 42 and a switching circuit 102. Switches 103a and 103b connected to the switching circuit 102 are alternately turned on/off. Accordingly, negative and positive current flows between the electrodes 41 and the indifferent electrode 34.

The multiplexer 42 is connected to ground (the substrate 43 in the present embodiment) through a capacitor 104. Further, a line for connecting the multiplexer 42 and the capacitor 104 is branched and connected to the input ports of comparators 101 and 106 through a buffer 105. The input port of the comparator 106 is connected to a line for connecting the capacitor 104 and the ground and the output port of the comparators 106 and 101 is connected to the switching circuit 102.

When the stimulation strength instruction signal and the electrode specifying signal generated by the converting circuit 100 are set in the switching circuit 102, the switching circuit 102 turns on the switch 103a. To this end, current flows in the electrode 41 selected by the multiplexer 42 and a voltage proportional to the charges is generated by the capacitor 104. The voltage generated by the capacitor 104 is detected by the comparator 101 through the buffer 105. When the voltage of the capacitor 104 is equal to the stimulation strength instruction signal, the comparator 101 is turned on and the switching circuit 102 turns off the switch 103a. In a next timing, the switching circuit 102 turns on the switch 103b and applies a reverse voltage. To this end, reverse (reverse polarity) current flows in the selected electrode 41 and the voltage of the capacitor 104 is reduced. The reduction in the voltage of the capacitor 104 is detected by the comparator 106. When the negative current and the positive current are substantially equal to each other, the voltage of the capacitor 104 is substantially reset to 0, the comparator 106 is turned on, and the switching circuit 102 turns off the switch 103b. The switch 103a and the switch 103b may be opposite to each other.

When the stimulation strength instruction signal is changed and the electrode specifying signal is set, the current flows in the selected electrode 41. When the direction of the current flowing between the electrode 41 and the indifferent electrode 34 is switched at a point of time when the voltage of the capacitor 104 is equal to the stimulation strength instruction signal and the voltage of the capacitor 104 is reset to 0, the charge injection amount is the same in the both polarities and the balance between the negative and positive charges is maintained. In addition, since the power supply voltage is applied to a biological body, it is possible to suppress power loss.

The image data of the object obtained by the photographing unit 12 is transmitted to the processing unit 13a. The processing unit 13a performs image processing on the received image data, converts the image data into the data for the electrostimulation pulse signal which is a predetermined data parameter necessary for allowing the patient to recognize the photographed object, and transmits the data for the electrostimulation pulse signal to the transmitting unit 14 as a modulation signal. In addition, the processing unit 13a converts the power from the power supply unit 13b into AC power having a radio frequency and transmits the AC power to the transmitting unit 14.

The controller 32 extracts the modulation signal from the signals received by the receiving unit 31, generates the stimulation strength instruction signal and the electrode specifying signal of the electrostimulation pulse signal based on the extracted modulation signal, and transmits the electrostimulation strength instruction signal and the electrode specifying signal to the multiplexer 42. The multiplexer 42 outputs the bipolar electrostimulation pulse signal from the electrodes 41 based on the received electrode specifying signal. Accordingly, the retina cell is subjected to the electrostimulation and the patient can obtain an optical vision (light perception).

What is claimed is:

1. A vision regeneration assisting apparatus for assisting a regeneration of a vision of a patient, comprising:
   a plurality of electrodes which are adapted to be placed in a human body of the patient to apply an electrostimulation pulse signal to a cell that forms a retina of the patient;
   a controller configured to apply power supply voltage to the plurality of electrodes to cause the plurality of electrodes to output the electrostimulation pulse signal having bipolarity; and
   a multiplexer configured to sequentially cause the plurality of electrodes to apply the electrostimulation pulse signal, wherein the controller comprises:
a capacitor connected to the multiplexer and adapted to accumulate a current which flows through the electrodes when the power supply voltage is applied to the electrodes and convert the current into a voltage, the current being used for the electrostimulation pulse signal for stimulating the cell of the retina;
a converting circuit configured to generate a stimulation strength instruction voltage value corresponding to a strength of the electrostimulation pulse signal;
a voltage detecting circuit which comprises a first comparator coupled to the converting circuit and the capacitor and configured to compare the voltage of the capacitor with the stimulation strength instruction voltage value which, and a second comparator coupled to the capacitor and configured to detect a decrease in the voltage of the capacitor; and
a switching circuit coupled to the detecting circuit and configured to connect a power supply source of a first polarity to one of the electrodes to allow the current of the first polarity to flow in the electrodes until the voltage of the capacitor reaches the stimulation strength instruction voltage value, based on the comparison result of the first comparator, and connect a power supply source of a second polarity to the one of the electrodes to allow the current having the second polarity, which is opposite to the first polarity, to flow in the electrodes until the voltage of the capacitor is substantially reset to 0 based on the detection result of the second comparator.

2. The vision regeneration assisting apparatus according to claim 1, wherein the voltage detecting circuit comprises a buffer configured to detect the voltage without affecting the voltage of the capacitor.

3. The vision regeneration assisting apparatus according to claim 2, wherein the multiplexer is configured to sequentially receive the electrostimulation pulse signals from the controller and output the electrostimulation pulse signals to the plurality of electrodes.

4. The vision regeneration assisting apparatus according to claim 1, further comprising:
a transmitting/receiving unit configured to transmit data for the electrostimulation pulse signal to the controller.

5. The vision regeneration assisting apparatus according to claim 4, further comprising:
a photographing unit configured to photograph an object to obtain image data; and
a processing unit configured to process the image data obtained by the photographing unit and convert the image data into the data for the electrostimulation pulse signal.

6. The vision regeneration assisting apparatus according to claim 1, further comprising:
a first switch configured to be turned on by the switching circuit for connecting the power supply source of the first polarity to the one of the electrodes disposed in the retina, to supply the current of the first polarity; and
a second switch configured to be turned on by the switching circuit, based on the comparison result of the first comparator, for connecting the power supply source of the second polarity to the one of the electrodes, to supply the current of the second polarity, when the first switch is off.

7. The vision regeneration assisting apparatus according to claim 1, wherein the switching circuit is configured to control one of a first switch and a second switch for connecting and applying the current of the first polarity and the second polarity, respectively, to one of the electrodes.

* * * * *